United States Patent
Weber

(10) Patent No.: US 8,744,568 B2
(45) Date of Patent: Jun. 3, 2014

(54) MEDICAL DEVICE WITH ELECTROACTIVE POLYMER POWERED BY PHOTOVOLTAIC CELL

(75) Inventor: Jan Weber, Maastricht (NL)

(73) Assignee: Boston Scientific Scimed, Inc., Maple Grove, MN (US)

( * ) Notice: Subject to any disclaimer, the term of this patent is extended or adjusted under 35 U.S.C. 154(b) by 426 days.

(21) Appl. No.: 12/953,807

(22) Filed: Nov. 24, 2010

(65) Prior Publication Data

US 2011/0152747 A1 Jun. 23, 2011

Related U.S. Application Data

(60) Provisional application No. 61/289,030, filed on Dec. 22, 2009.

(51) Int. Cl.
*A61N 1/30* (2006.01)
*A61M 31/00* (2006.01)
*A61K 9/22* (2006.01)

(52) U.S. Cl.
USPC .......... 604/20; 604/21; 604/501; 604/890.1; 604/891.1

(58) Field of Classification Search
USPC .......... 604/20, 21, 22, 501, 891.1, 890.1, 500
See application file for complete search history.

(56) References Cited

U.S. PATENT DOCUMENTS

| | | | |
|---|---|---|---|
| 4,585,652 A | 4/1986 | Miller et al. | |
| 5,100,523 A | 3/1992 | Helms et al. | |
| 5,387,189 A * | 2/1995 | Gory et al. | 604/20 |
| 6,185,452 B1 * | 2/2001 | Schulman et al. | 604/20 |
| 6,921,360 B2 | 7/2005 | Banik | |
| 6,969,395 B2 | 11/2005 | Eskuri | |
| 7,203,548 B2 * | 4/2007 | Whitehurst et al. | 607/39 |
| 7,338,509 B2 | 3/2008 | Mattison | |
| 7,431,692 B2 * | 10/2008 | Zollinger et al. | 600/37 |
| 7,572,625 B2 | 8/2009 | Davis et al. | |
| 2002/0022795 A1 * | 2/2002 | Reynolds et al. | 604/20 |
| 2002/0116033 A1 | 8/2002 | Greatbatch et al. | |
| 2004/0176673 A1 * | 9/2004 | Wahlstrand et al. | 600/377 |
| 2005/0196421 A1 | 9/2005 | Hunter et al. | |
| 2005/0227373 A1 * | 10/2005 | Flandre et al. | 436/518 |
| 2008/0004564 A1 | 1/2008 | Smith | |
| 2008/0262412 A1 * | 10/2008 | Atanasoska et al. | 604/20 |

OTHER PUBLICATIONS

Cervini, et al., "Solid-state Ru-dye solar cells using polypyrrole as a hole conductor," J. Phys. D: Appl. Phys. 37 (2004), pp. 13-20.

(Continued)

*Primary Examiner* — Emily Schmidt
*Assistant Examiner* — Lauren M Peng
(74) *Attorney, Agent, or Firm* — Fish & Richardson P.C.

(57) ABSTRACT

Medical devices comprising an electroactive polymer powered by a photovoltaic cell. In one embodiment, the medical device has an electroactive component comprising an electroactive polymer. The medical device further comprises a photovoltaic cell as a source of electrical power for electrically stimulating the electroactive polymer. The medical device further comprises a first electrode and a second electrode, both of which are electrically connected to the photovoltaic cell. The electroactive component covers over at least a portion of the first electrode. Also disclosed is a method of treating a patient using a medical device having an electroactive polymer powered by a photovoltaic cell.

19 Claims, 2 Drawing Sheets

(56) References Cited

OTHER PUBLICATIONS

Cui et al., "Surface modification of neural recording electrodes wtih conducting polymer/biomolecule blends," J Biomed Mater Res. (2001), pp. 261-272, John Wiley & Sons, Inc.

Cui et al., "Fuzzy gold electrodes for lowering impedance and improving adhesion with electrodeposited conducting polymer films," Sensors & Actuators A, vol. 103 (2003), pp. 384-394.

Fujisue, "Work behaviors of artificial muscle based on cation driven polypyrrole," Bioinsp. Biomim. 2 (2007), S1-S5.

Song et al., "A microscale photovoltaic neurostimulator for fiber optic delivery of functional electrical stimulation," J. Neural Eng., vol. 4 (2007), pp. 213-218.

Thompson et al., "Optimising the incorporation and release of a neurotrophic factor using conducting polypyrrole," Journal of Controlled Release 116 (2006), pp. 285-294.

Wadhwa et al. "Electrochemically controlled release of dexamethasone from conducting polymer polypyrrole coated electrode," Journal of Controlled Release 110 (2006), pp. 531-541.

\* cited by examiner

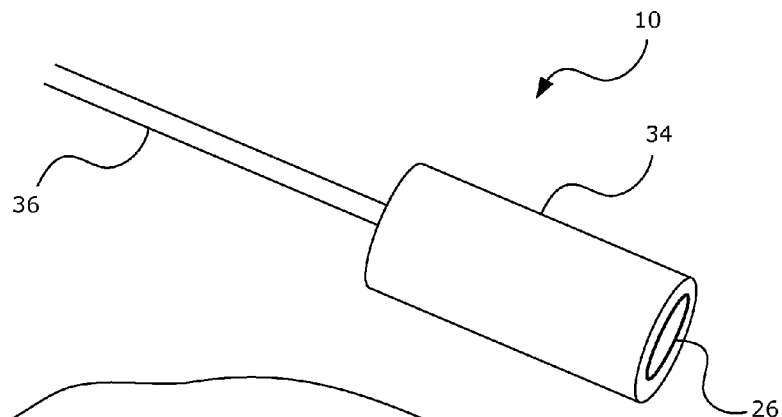
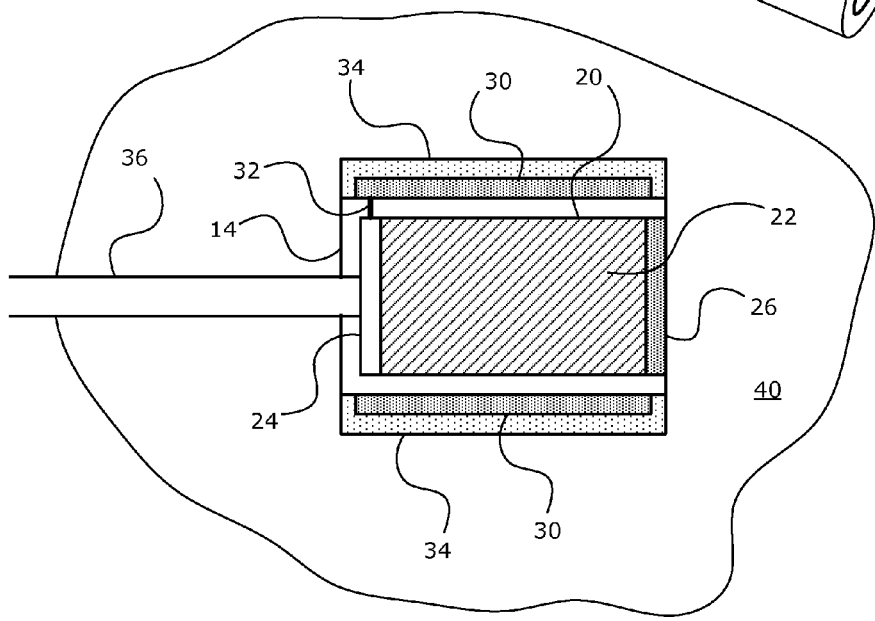
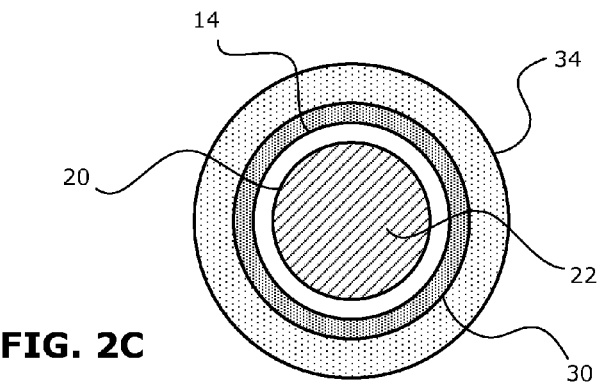

US 8,744,568 B2

MEDICAL DEVICE WITH ELECTROACTIVE POLYMER POWERED BY PHOTOVOLTAIC CELL

CROSS REFERENCE TO RELATED APPLICATION

The present application claims priority to U.S. provisional application Ser. No. 61/289,030 filed Dec. 22, 2009, the disclosure of which is incorporated herein by reference in its entirety.

TECHNICAL FIELD

The present invention relates to medical devices that use an electroactive polymer.

BACKGROUND

There is increasing interest in the use of electroactive polymers in medical devices. For example, electroactive polymers can be used to make implantable actuators that can be controlled by electrical stimulation. In such medical devices, the electroactive polymer requires a source of electrical power. For implanted medical devices, where the power supply is external to the patient, the electroactive polymer can be connected to the external power supply via an electrical lead (e.g., through a catheter). Another approach is to provide the implanted medical device with a receiver coil connected to the electroactive polymer and provide electrical power by inductive coupling with an externally located transmitter coil. However, both of these approaches can cause problems when the patient is subjected to an MRI examination. In particular, the powerful RF fields generated by an MRI machine can produce inductive currents in the electrical leads or coils. Heating of the leads or coils by the induced current can cause injury to the patient.

Another approach for providing a power supply is to implant a battery along with the medical device. However, this approach requires the implantation of another component into the patient's body (batteries can be bulky) and risks the possibility of potentially toxic chemicals leaking from the battery. Thus, there is a need for an alternative power supply for medical devices using electroactive polymers.

SUMMARY

The medical devices disclosed herein comprise an electroactive polymer in which electrical power is supplied by a photovoltaic cell. In one embodiment, the present invention provides a medical device comprising: (a) photovoltaic cell; (b) a first electrode electrically connected to the photovoltaic cell; (c) a second electrode electrically connected to the photovoltaic cell; and (d) an electroactive component covering over the first electrode, wherein the electroactive component comprises an electroactive polymer.

In another embodiment, the present invention provides a method of treating a patient, comprising: implanting a medical device into the patient's body, the medical device comprising: (a) a photovoltaic cell, (b) a first electrode electrically connected to the photovoltaic cell, (c) a second electrode electrically connected to the photovoltaic cell, and (d) an electroactive component covering over the first electrode, wherein the electroactive component comprises an electroactive polymer; and exposing the photovoltaic cell to light to electrically stimulate the electroactive polymer in the electroactive component.

BRIEF DESCRIPTION OF THE DRAWINGS

FIG. 1A shows an electroactive polymer coating with a therapeutic agent loaded therein; and FIG. 1B shows the electroactive polymer coating with the therapeutic agent released.

FIGS. 2A-2C show a medical device according to an embodiment of the present invention. FIG. 2A shows a perspective view; FIG. 2B shows a longitudinal cross-section view; and FIG. 2C shows a transverse cross-section view.

DETAILED DESCRIPTION

Figure 1A:
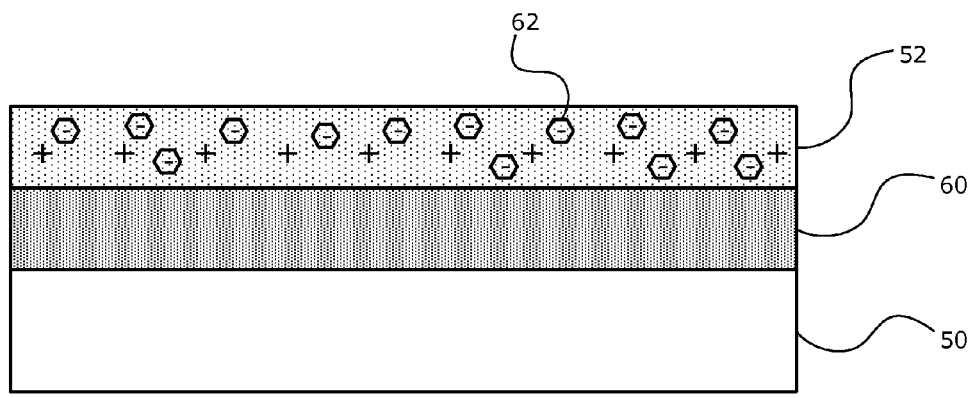
FIGS. 1A and 1B show an example of how electroactive polymers can be used for controlled release of a therapeutic agent.

In one embodiment, the present invention provides a medical device having an electroactive component comprising an electroactive polymer. The medical device further comprises a photovoltaic cell as a source of electrical power for electrically stimulating the electroactive polymer. The medical device further comprises a first electrode and a second electrode, both of which are electrically connected to the photovoltaic cell. The electroactive component covers over at least a portion of the first electrode.

As used herein, "electroactive polymer" means a polymer that can undergo an electrochemical change (i.e., oxidation or reduction) by the application of an electrical potential. As such, the polymer can be made to undergo redox cycling by electrical stimulation. Representative examples of electroactive polymers include polyaniline, polythiophene, polypyrrole, and polyacetylene. In electroactive polymers, the oxidation or reduction of the polymer involves the movement of ionic species into and out of the polymer material. As such, in many cases, electroactive polymers can undergo shape changes caused by volume expansion or contraction with the flow of water into or out of the polymer material in conjunction with the movement of ions. Many electroactive polymers are electrically conductive or semi-conductive and are characterized by having π-conjugated double-bonds along the backbone of the polymer to provide a conductive pathway along the polymer chain.

The electroactive component may be made of the electroactive polymer alone, or may also include other materials, such as therapeutic agents or other additives as described below. The electroactive component can be any functional component of a medical device, such as an actuator or a reservoir for a therapeutic agent. Examples of electroactive polymer actuators include those described in U.S. Pat. No. 6,969,395 (Boston Scientific SciMed; "Electroactive polymer actuated medical devices"), U.S. Pat. No. 6,921,360 (Boston Scientific SciMed; "Electroactive polymer based artificial sphincters and artificial muscle patches"), and U.S. Pat. No. 7,338,509 (Boston Scientific SciMed; "Electroactive polymer actuated sheath for implantable or insertable medical device"), all three of which are incorporated by reference herein. The electroactive component can have any of various structural forms, depending upon its function. For example, the electroactive component may be in the form of a coating layer, strip, bar, or patch. In some cases, the electroactive component is a coating layer functioning as a reservoir for a therapeutic agent.

In certain embodiments, the electroactive component comprises a therapeutic agent with the electroactive polymer being used for controlled release of the therapeutic agent. The electrochemical oxidation or reduction of the polymer involves the movement of ionic species into or out of the polymer material. Thus, in some cases, the therapeutic agent may be an ionic species. By incorporating the therapeutic agent as an ionic additive in the polymer matrix of the electroactive component, the redox chemistry of the polymer can be used to release the therapeutic agent.

The therapeutic agent may be incorporated into the electroactive component in various ways. In some cases, the therapeutic agent is dispersed in the electroactive component and ionically bonded to the electroactive polymer. For example, the therapeutic agent may be loaded into the electroactive component during the polymerization process of the electroactive polymer. For example, the monomers may be electropolymerized in the presence of a salt of the ionic therapeutic agent. In this process, the polymers are made in an oxidized or reduced state with the ionic therapeutic agent held in the polymer matrix by the ionic interaction with the charged electroactive polymers. Thus, the therapeutic agent acts as a counterion that neutralizes the overall charge. When the charge on the electroactive polymers is reversed or neutralized, the therapeutic agent counterions are released from the polymer matrix.

Both anionic and cationic species of therapeutic agents can be held in the polymer matrix. For example, cationic species can be incorporated by synthesizing the polymer using a large immobile polyanion, such as poly(vinyl-sulfonate). When the polymer is reduced, the large polyanions are trapped in the polymer so that cations in the surrounding electrolyte are incorporated into the polymer to balance the charge of the polyanion. The therapeutic agent may also be incorporated into the polymer matrix by covalent bonding, with cleavage of the bond by the electrically-induced oxidation/reduction changes.

Figure 1B:
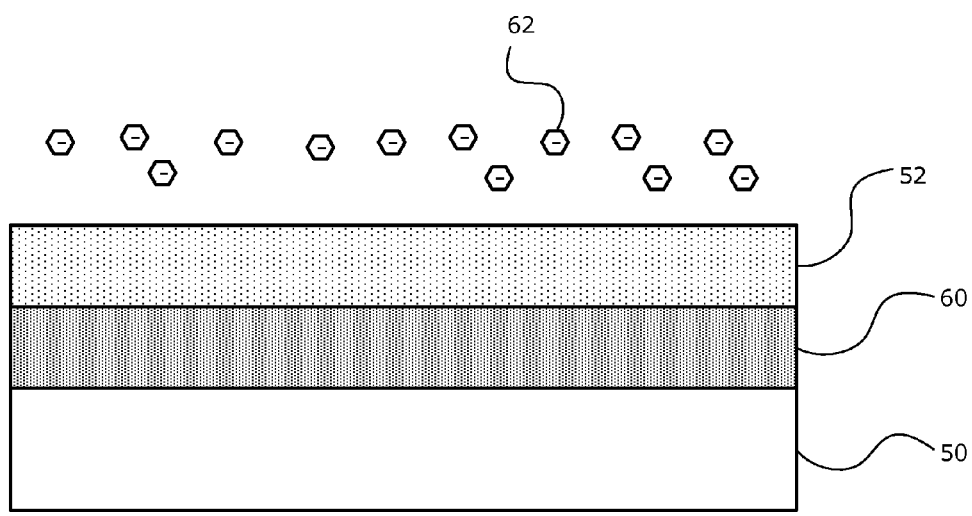

FIGS. 1A and 1B show an example of how an electroactive polymer may be used for controlled release of a therapeutic agent. In FIG. 1A, a medical device 50 has a coating 52 comprising an polypyrrole polymer and a therapeutic agent 62 (as an anionic species). Coating 52 is disposed on a metal electrode 60. Coating 52 is made by electropolymerizing pyrrole monomers in the presence of a salt of the anionic therapeutic agent 62. As a result, the polypyrrole coating 52 is made with the polypyrrole polymers having a positive electrostatic charge (represented by the "+" signs) and the anionic therapeutic agent 62 is held within the polymer matrix by ionic attraction to the positively-charged moieties on the polypyrrole polymers.

As shown in FIG. 1B, when release of the anionic therapeutic agent 62 is desired, an electrical potential is applied to the polypyrrole coating 52 by electrode 60. As a result, the polypyrrole polymers in coating 52 undergo an electrochemical change such that the electrostatic charges on the electroactive polymers are neutralized. Freed from the ionic attraction to the polypyrrole polymers, the anionic therapeutic agent 62 is released from coating 52.

The therapeutic agent does not necessarily have to be an ionic species in order for the medical device to be operative. In some cases, the electroactive component and/or therapeutic agent may be designed such that a volume change in the electroactive polymer causes the release of the therapeutic agent. For example, the electroactive component may have voids for containing the therapeutic agent (whether ionic or non-ionic), whereby swelling of the electroactive polymer induced by redox switching causes the therapeutic agent to be released from the voids.

The photovoltaic cell, which can be used for electrically stimulating the electroactive polymer, converts light energy into electrical energy. The photovoltaic cell may be any suitable photovoltaic cell known in the art. Typically, a photovoltaic cell has a positive terminal, a negative terminal, and a semiconductor portion (e.g., made with gallium-arsenide) between the two terminals where the photoelectric activity takes place. The photovoltaic cell is capable of generating a voltage potential sufficient to active an electroactive polymer. In some cases, the photovoltaic cell is capable of generating a potential difference of 0.5 volts or greater (negative or positive); and in some cases, in the range of 0.5-10 volts. Voltage potentials in this range may be capable of activating an electroactive polymer while avoiding excessively high current flows through the physiologic fluid. Other voltage potentials may also be generated by the photovoltaic cell.

The photovoltaic cell requires a source of light in order to produce electrical energy. The light source for the photovoltaic cell can be provided in a variety of ways. In some cases, the light source may be located remote from the medical device (e.g., outside the body) and the light from the source is guided to the photovoltaic cell by an optical fiber, which may be operatively coupled to the photovoltaic cell. The optical fiber may or may not be capable of being decoupled from the medical device. Any suitable light source may be used, including a laser or a light-emitting diode. In some cases, the medical device is designed for implantation near the external surface of the body (e.g., under the skin) where it can receive light that is transmitted directly into the body (e.g., through the skin).

In certain embodiments, the photovoltaic cell is contained inside an insulative housing for electrical and/or environmental isolation. The insulative housing may be made from any suitable non-conductive or low-conductive material, including polymers and ceramics (e.g., silica, zirconium oxide, or other metal oxides) that are suitable for implantation in the body. In embodiments where the photovoltaic cell is contained inside a housing, the medical device may include one or more electrodes located outside the housing that are electrically connected to the positive and/or negative terminals of the photovoltaic cell.

The first and second electrodes of the medical device may be any of the photovoltaic cell terminals and/or electrodes described above. In some cases, the first electrode may be the positive or the negative terminal of the photovoltaic cell. In some cases, the second electrode may be the positive terminal or the negative terminal of the photovoltaic cell. For embodiments where the photovoltaic cell is contained in an insulative housing, in some cases, the first and/or second electrode may be an externally located electrode on the housing. In some cases, one of the first or second electrodes is the positive terminal or negative terminal of the photovoltaic cell, and the other of the first or second electrodes is an externally located electrode on the housing.

The electroactive component covers over at least a portion of the first electrode. The electroactive component may or may not be in direct physical contact with the first electrode. In some cases, the electroactive component completely covers over the first electrode to avoid creating short circuit pathways between the first and second electrodes. In some cases, the electroactive component uniformly covers over the first electrode (e.g., as a layer of uniform thickness) to allow a more uniform current flow through the electroactive component. In embodiments where the electroactive component contains a therapeutic agent, this feature may provide the benefit of a more uniform release of the therapeutic agent across the electroactive component.

The second electrode is configured to be in electrical contact with physiologic fluid or body tissue when the medical device is implanted. The second electrode may or may not be in direct physical contact with the physiologic fluid or body tissue. For example, the second electrode may be exposed (i.e., designed for direct physical contact with the physiologic fluid or body tissue) or have a protective film that is sufficiently thin to allow the passage of current from the second electrode to the physiologic fluid or body tissue.

The first and second electrodes may comprise any suitable electrically conductive material, including metals, carbon, or electrically conductive polymers. In some cases, the first electrode functions as the working electrode and the second electrode functions as the counter electrode when the medical device is activated in an electrolyte fluid (e.g., in physiologic fluid inside a patient's body). In this configuration, current flows between the two electrodes through the electrolyte fluid. This function may also be determined by immersing the housing in an electrolyte fluid made for testing purposes (e.g., in a laboratory beaker). In some cases, the first and/or second electrodes comprise an electrochemically inert, electrically conductive material. Representative examples of such materials include gold, platinum, or inert carbon (e.g., glassy carbon, graphite, or pyrolytic carbon).

The use of electrochemically inert materials for the first and/or second electrodes may cause the electrolysis of water, with the resultant production of $H_2$ and/or $O_2$ gases. In situations where such byproducts are undesirable, the first and/or second electrodes may be made of a material that is electrochemically reactive such that the electrode(s) themselves undergo oxidation or reduction during the operation of the medical device. In such cases, the electrode(s) itself would be oxidized or reduced and the electrolysis of water can be avoided or minimized. Representative examples of electrochemically reactive conductive materials include silver, zinc, copper, nickel, iron, silver chloride, and silver bromide.

A specific example of a medical device according to one particular embodiment of the present invention is shown in FIGS. 2A (perspective view), 2B (longitudinal cross-section view), and 2C (transverse cross-section end view). Implantable medical device 10, which functions as a subcutaneous drug depot, comprises a conventional photovoltaic cell 20 that is sealed within an insulative zirconium oxide housing 14. Photovoltaic cell 20 includes a semiconductor portion 22 made using a gallium-arsenide semiconductor material (see, e.g., Song et al., "A microscale photovoltaic neurostimulator for fiber optic delivery of functional electrical stimulation," J. Neural Eng., vol. 4, pp. 213-218 (2007)).

Photovoltaic cell 20 also includes a negative terminal 24 and a metal base 26 (representing a second electrode), which is the positive terminal of photovoltaic cell 20. Metal base 26 (positive terminal) also serves to seal photovoltaic cell 20 within titanium housing 14. Metal base 26 is exposed to the physiologic fluid when medical device 10 is implanted. Photovoltaic cell 20 and housing 14 are mounted on the end of a catheter 36, which contains a fiber optic line that is operatively coupled to photovoltaic cell 20. At its other end, the fiber optic line is coupled to an external light source.

A thin film of gold is deposited onto housing 14 by pulsed laser deposition to form a gold electrode 30 (representing a first electrode). Gold electrode 30 is electrically connected to the negative terminal 24 via a sealed contact 32 through housing 14. Disposed on gold electrode 30 is a coating layer 34 of uniform thickness made of polypyrrole (representing an electroactive polymer) and containing an anionic therapeutic agent dispersed within the polymer matrix. Coating layer 34 completely covers over the gold electrode 30 to avoid creating short circuits to gold electrode 30. Coating layer 34 is made by oxidative electropolymerization on gold electrode 30 using pyrrole monomers in the presence of the anionic therapeutic agent.

In operation, medical device 10 is implanted in a patient's body. For example, the device may be implanted subcutaneously near the collar bone on the side of the patient's neck, which can allow convenient attachment to a light source. In the patient's body, the distal portion of medical device 10 is surrounded by physiologic fluid 40 (see FIG. 2B). When the external light source is activated, the light energy is carried through the fiber optic line in catheter 36 to illuminate photovoltaic cell 20. When illuminated, photovoltaic cell 20 generates a voltage potential, which is applied to gold electrode 30 and metal base 26. With the application of a voltage potential by photovoltaic cell 20, current flows between gold electrode 30 and metal base 26 through coating layer 34 via physiologic fluid 40. The electrical stimulation of the polypyrrole polymers in coating layer 34 causes the release of the therapeutic agent. Catheter 36 is detachable such that housing 14 and its associated components remain implanted in the patient's body.

The therapeutic agent may be an anionic, cationic, or neutral species. Examples of anionic therapeutic agents useful as counterions include compounds that are salts of carboxylates, phosphates, sulfates, bisulfates, and salts of acidic N—H moieties, such as amides. Therapeutic agents containing these functional groups may be available as their water-soluble alkali metal or alkaline earth metal salts, such as sodium, lithium, potassium, magnesium, or calcium salts. Examples of cationic therapeutic agents useful as counterions include halide, nitrate, or methylsulfate salts of quaternary amines, and charged sulfur or nitrogen-containing heterocyclic drugs. Neutrally-charged therapeutic agents may be modified to introduce a suitable ionic functional group into the molecule, such as the above-mentioned phosphates, sulfates, quaternary amines, etc.

Upon implantation of the medical device, the physiologic fluid in the body serves as the electrolyte material. However, implantation of medical devices can cause a tissue reaction, which can result in scar tissue that encapsulates the implanted device. Tissue encapsulation of the medical device may limit the amount of physiologic fluid available to serve as the electrolyte material. To alleviate this problem, the electroactive component may further comprise a fibrosis-inhibiting agent, which can be the therapeutic agent itself, or in addition to the therapeutic agent (i.e., the electroactive component comprises a first therapeutic agent and the fibrosis-inhibiting agent as a second therapeutic agent). The fibrosis-inhibiting agent serves to reduce the amount of tissue reaction caused by the implanted medical device, thus prolonging the availability of electrolyte material for the medical device to continue operating.

Examples of fibrosis-inhibiting agents include those described in U.S. Patent Application Publication No. 2005/0196421 (Hunter et al., "Polymer compositions and methods for their use"). As explained therein, the fibrosis-inhibiting agents inhibit tissue fibrosis through one or more mechanisms including: inhibiting inflammation or the acute inflammatory response, inhibiting migration or proliferation of connective tissue cells (such as fibroblasts, smooth muscle cells, or vascular smooth muscle cells), inhibiting angiogenesis, reducing extracellular matrix (ECM) production or promoting ECM breakdown, and/or inhibiting tissue remodeling. Such fibrosis-inhibiting agents include anti-inflammatory agents, which include corticosteroids (natural or synthetic) and non-steroidal anti-inflammatory agents. Representative examples of corticosteroids include beclomethasone, betamethasone, cortisone, dexamethasone, fluocinolone, fluocinonide, hydrocortisone, methylprednisolone, prednisolone, prednisone, and triamcinolone. Representative examples of non-steroidal anti-inflammatory agents include ibuprofen, naproxen, diclofenac, and licofelone.

The ion exchange that takes place with the electrochemical changes to the electroactive polymer may cause the polymer to swell or contract. This volume change may promote cracking and/or delamination of the electroactive component off of the electrode. Thus, the medical device may be designed to increase adhesion between the electroactive component and the electrode, which may be achieved in various ways. In certain embodiments, the first electrode has rough surface to improve adhesion of the electroactive polymer. In some cases, the rough surface of the electrode has an average grain size (along its longest axis) in the range of 200 nm to 5 μm.

An electrode having a rough surface can be made using any suitable technique. For example, the surface of the electrode may be roughened by patterning, etching, sand blasting, chemical treatments, etc. Also, the electrode itself may be fabricated in a manner that provides a rough surface. For example, Cui et al., "Fuzzy gold electrodes for lowering impedance and improving adhesion with electrodeposited conducting polymer films," Sensors & Actuators A, vol. 103, pp. 384-394 (2003) describes an electroplating technique for making an electrode having a rough surface.

In certain embodiments, the electroactive component includes a pharmaceutically-acceptable binder to improve adhesion with the first electrode. Representative examples of pharmaceutically-acceptable binders include polyvinyl pyrrolidone (PVP), hydroxypropyl cellulose, hydroxypropyl methylcellulose, methylcellulose, sugars, and starches. In certain embodiments, an adhesion promoting layer is interposed between the electroactive component and the electrode. The adhesion promoting layer comprises a material that enhances the adhesion between the electroactive polymers and the electrode. Examples of materials that can be used for the adhesion promoting layers include p-aminothiophenol, indium-tin oxide, and amorphous carbon, as disclosed in U.S. Pat. No. 5,100,523, which is incorporated by reference herein. The thickness of the adhesion promoting layer may be in the range of 3 nm-100 nm, but other thicknesses are also possible.

In certain embodiments, the first electrode is pre-treated to increase the interfacial cohesion between the electrode and the electroactive polymer. Examples of such treatments include mechanical abrasion, chemical treatments (e.g., exposure to oxidizing agents or surface activation by introduction of functional groups), or physical-chemical treatment (e.g., exposure to plasma or UV radiation).

In certain embodiments, at least a portion of the medical device is designed to be implantable. For example, the implantable portion may include the photovoltaic cell, its housing, the first and second electrodes, and the electroactive component. Where the medical device includes a fiber optic line, the fiber optic line may or may not be part of the implantable portion. In some cases, the entire medical device is designed to be implantable.

The implantable portion of the medical device may include other electrical components. For example, the implantable portion may include a capacitor to store electrical charge generated by the photovoltaic cell. Capacitors, including supercapacitors, can provide electrical power when the photovoltaic cell is decoupled from the light source. The implantable portion may also include circuitry for the regulation of voltage, current, and/or power applied to the first and/or second electrodes.

Non-limiting examples of medical devices according to the present invention include catheters, guide wires, balloons, filters (e.g., vena cava filters), stents, stent grafts, vascular grafts, intraluminal paving systems, pacemakers, electrodes, leads, defibrillators, joint and bone implants, spinal implants, access ports, intra-aortic balloon pumps, heart valves, sutures, artificial hearts, neurological stimulators, cochlear implants, retinal implants, and other devices that can be used in connection with therapeutic coatings. Such medical devices are implanted or otherwise used in body structures, cavities, or lumens such as the vasculature, gastrointestinal tract, abdomen, peritoneum, airways, esophagus, trachea, colon, rectum, biliary tract, urinary tract, prostate, brain, spine, lung, liver, heart, skeletal muscle, kidney, bladder, intestines, stomach, pancreas, ovary, uterus, cartilage, eye, bone, joints, and the like.

The therapeutic agent used in the present invention may be any pharmaceutically acceptable agent (such as a drug), a biomolecule, a small molecule, or cells. Exemplary drugs include anti-proliferative agents such as paclitaxel, sirolimus (rapamycin), tacrolimus, everolimus, biolimus, and zotarolimus. Exemplary biomolecules include peptides, polypeptides and proteins; antibodies; oligonucleotides; nucleic acids such as double or single stranded DNA (including naked and cDNA), RNA, antisense nucleic acids such as antisense DNA and RNA, small interfering RNA (siRNA), and ribozymes; genes; carbohydrates; angiogenic factors including growth factors; cell cycle inhibitors; and anti-restenosis agents. Exemplary small molecules include hormones, nucleotides, amino acids, sugars, and lipids and compounds have a molecular weight of less than 100 kD. Exemplary cells include stem cells, progenitor cells, endothelial cells, adult cardiomyocytes, bone marrow cells, and smooth muscle cells. Other therapeutic agents that may be used in the present invention include those listed in U.S. Pat. No. 7,572,625 (Davis et al., "Medical devices coated with drug carrier macromolecules"), which is incorporated by reference herein. Any of the therapeutic agents may be combined to the extent such combination is biologically compatible.

The foregoing description and examples have been set forth merely to illustrate the invention and are not intended to be limiting. Each of the disclosed aspects and embodiments of the present invention may be considered individually or in combination with other aspects, embodiments, and variations of the invention. Modifications of the disclosed embodiments incorporating the spirit and substance of the invention may occur to persons skilled in the art and such modifications are within the scope of the present invention.

What is claimed is:

1. A medical device comprising:
   a photovoltaic cell;
   an insulative housing that contains the photovoltaic cell;
   a first electrode electrically connected to the photovoltaic cell and located on an outer surface of the housing;
   a second electrode electrically connected to the photovoltaic cell and exposed to an external environment;
   an electroactive component covering over the first electrode, wherein the electroactive component comprises an electroactive polymer;
   a catheter coupled to the housing; and
   a fiber optic line contained in the catheter and operatively coupled to the photovoltaic cell.

2. The device of claim 1, wherein the electroactive component completely covers over the first electrode.

3. The device of claim 2, wherein the electroactive component uniformly covers over the first electrode.

4. The device of claim 1, wherein both the first and second electrodes comprise an electrochemically inert material.

5. The device of claim 1, wherein the first electrode, the second electrode, or both comprise an electrochemically reactive material.

6. The device of claim 1, wherein the medical device is adapted such that immersion of the medical device in an electrolyte fluid causes the first electrode and the second electrode to be electrically connected via the electrolyte fluid.

7. The device of claim 1, wherein the electroactive component further comprises a therapeutic agent.

8. The device of claim 1, wherein the electroactive component is an actuator.

9. The device of claim 1, wherein at least a portion of the medical device is implantable, and wherein the implantable portion includes the photovoltaic cell, the first and second electrodes, the insulative housing, and the electroactive component.

10. The device of claim 1, wherein the first electrode has a rough surface.

11. The device of claim 10, wherein the rough surface has an average grain size in the range of 200 nm to 5 µm.

12. The device of claim 1, wherein the electroactive component further comprises a fibrosis-inhibiting agent.

13. The device of claim 12, wherein the fibrosis-inhibiting agent is an anti-inflammatory agent.

14. The device of claim 1, wherein the photovoltaic cell is capable of generating a potential of 0.5 volts or greater.

15. The device of claim 1, wherein the second electrode is the positive or negative terminal of the photovoltaic cell.

16. A method of treating a patient, comprising:
implanting a medical device into the patient's body, the medical device comprising:
(a) a photovoltaic cell contained in an insulative housing;
(b) a first electrode electrically connected to the photovoltaic cell and located on an outer surface of the housing;
(c) a second electrode electrically connected to the photovoltaic cell and exposed to an external environment;
(d) an electroactive component covering over the first electrode, wherein the electroactive component comprises an electroactive polymer;
(e) a catheter coupled to the housing; and
(f) a fiber optic line contained in the catheter and operatively coupled to the photovoltaic cell; and
exposing the photovoltaic cell to light to electrically stimulate the electroactive polymer in the electroactive component.

17. The method of claim 16, further comprising applying a fibrosis-inhibiting agent at the implantation site.

18. The method of claim 16, further comprising releasing a therapeutic agent from the electroactive component.

19. The method of claim 16, further comprising inducing a current between the first electrode and the second electrode through physiologic fluid in the patient's body.

* * * * *

UNITED STATES PATENT AND TRADEMARK OFFICE
CERTIFICATE OF CORRECTION

PATENT NO. : 8,744,568 B2  
APPLICATION NO. : 12/953807  
DATED : June 3, 2014  
INVENTOR(S) : Jan Weber Page 1 of 1

It is certified that error appears in the above-identified patent and that said Letters Patent is hereby corrected as shown below:

Title Page 2, item (56) Col. 1, Line 5, Delete "wtih" and insert --with--, therefor.

Signed and Sealed this
Sixteenth Day of September, 2014

Michelle K. Lee
*Deputy Director of the United States Patent and Trademark Office*